(12) United States Patent
Silverman

(10) Patent No.: US 10,345,221 B1
(45) Date of Patent: *Jul. 9, 2019

(54) ULTRASONIC CORROSION COUPON PROBE

(71) Applicant: BERKELEY SPRINGS INSTRUMENTS LLC, Cumberland, MD (US)

(72) Inventor: Eugene B. Silverman, Great Cacapon, WV (US)

(73) Assignee: BERKELEY SPRINGS INSTRUMENTS LLC, Cumberland, MD (US)

( * ) Notice: Subject to any disclaimer, the term of this patent is extended or adjusted under 35 U.S.C. 154(b) by 435 days.

This patent is subject to a terminal disclaimer.

(21) Appl. No.: 14/757,435

(22) Filed: Dec. 23, 2015

Related U.S. Application Data

(60) Provisional application No. 62/096,242, filed on Dec. 23, 2014.

(51) Int. Cl.
| | | |
|---|---|---|
| *G01N 17/04* | (2006.01) | |
| *G01N 29/22* | (2006.01) | |
| *G01B 17/02* | (2006.01) | |
| *G01N 29/07* | (2006.01) | |

(52) U.S. Cl.
CPC .......... *G01N 17/046* (2013.01); *G01B 17/02* (2013.01); *G01N 29/07* (2013.01); *G01N 29/223* (2013.01)

(58) Field of Classification Search
CPC .... G01N 17/046; G01N 17/043; G01N 29/07; G01N 29/223; G01N 29/2468; G01B 17/02

USPC ..... 73/627, 597, 598, 590, 594, 601, 86, 87, 73/432.1
See application file for complete search history.

(56) References Cited

U.S. PATENT DOCUMENTS

| | | | | |
|---|---|---|---|---|
| 3,056,284 | A | * 10/1962 | Marsh | G01N 17/04 324/700 |
| 3,747,398 | A | * 7/1973 | Rathburn | G01B 17/00 73/617 |
| 5,636,959 | A | * 6/1997 | Kroell | B63B 17/023 114/201 R |
| 2002/0078752 | A1 * | 6/2002 | Braunling | G01N 17/04 73/627 |
| 2002/0148293 | A1 * | 10/2002 | Little | G01N 29/11 73/579 |
| 2016/0109413 | A1 * | 4/2016 | Bonadies, Jr. | G01N 29/07 73/598 |
| 2017/0067736 | A1 * | 3/2017 | Silverman | G01B 17/02 |

FOREIGN PATENT DOCUMENTS

JP          62266457 A    * 11/1987

* cited by examiner

*Primary Examiner* — Lisa M Caputo
*Assistant Examiner* — Rose M Miller
(74) *Attorney, Agent, or Firm* — Birch, Stewart, Kolasch & Birch, LLP

(57) ABSTRACT

A sacrificial metal coupon is provided with one or more ultrasonic transducers which, when excited by a pulser-receiver excitation pulse, determines the thickness of the coupon and its rate of change over time. The sacrificial metal coupon ultrasonic transducer assembly can be inserted into the liquid stream of a pipe, under or inside of a tank, underground or underwater, or inserted into structures where absolute material loss values or material loss rate of change is being monitored.

2 Claims, 8 Drawing Sheets

ULTRASONIC CORROSION COUPON PROBE

CROSS REFERENCE TO RELATED APPLICATIONS

This application claims the benefit of U.S. provisional application No. 62/096,242, filed Dec. 23, 2014, the contents of which are incorporated herein by reference.

FIELD OF INVENTION

This application relates to measuring and testing, and more specifically it relates to erosion and corrosion monitoring using a sacrificial coupon.

BACKGROUND

Corrosion will reduce the useful life of a structure. Corrosion may result in the thinning of the structure, pitting of the structure, or cracking of the structure. The type of corrosion that may occur and the type of corrosion monitoring systems needed to assess the degree of corrosion will depend on the service environment of the structure and the condition and operational use of the structure. There are three basic approaches to corrosion monitoring. The first is to make a "direct" measurement of the physical properties of the structure itself. The second is to use a "surrogate" material positioned in the service area, which is identical to the material in the structure, and infer the corrosion of the structure from the surrogate material. The third is to monitor the "chemistry" of the solution or gas upstream, downstream or within the service environment and then infer the effects of corrosion on the structure from an empirical or theoretical relationship that relates the measured quantity to the corrosion-induced damage.

The objective of all three corrosion-monitoring methods is to predict the remaining useful life of the structure of interest from an estimate of the corrosion measured or inferred with the monitoring method. In the case of monitoring the structure directly, a simple extrapolation can be made once several time-sequenced measurements have been made. In the case of either monitoring corrosive chemistry or monitoring surrogates, an inference must be made that correlates the corrosion measurement taken to the actual impacts on the structure.

Direct monitoring is a preferred method, but due to access, safety, or cost implications, this approach is not always viable. Direct monitoring may involve visual or photographic inspection of the structure, or physical measurements of the dimensions of the structure, e.g., wall thickness; pit depth, diameter or pit density; or crack depth, width, length or density. The main problem with direct monitoring is the access to the structure is needed and in many instances, access is not possible. Such measurements cannot be practically be made, for example, in radioactive storage containers, or on the walls of underground or the floor of aboveground storage tanks and piping containing petroleum or other hazardous substances and hazardous waste. For these types of applications, surrogate monitoring and chemistry monitoring systems are normally employed.

There are commercially available corrosion monitoring techniques that involve direct monitoring of a surrogate. The surrogate material is typically made of the same material as the structure of interest. The most common surrogate monitoring approach is the direct placement of corrosion coupons in the environment of interest. A corrosion coupon is a piece of material similar, or preferably identical to, the material of interest. The corrosion coupon(s) are placed in similar service conditions and then removed from the service area and evaluated at a later date. These coupon inspections are done periodically and are not linked to a specific level of corrosion. The coupons may be analyzed using destructive metallography. They may be inspected for appearance and/or weighed and compared to the pre-service weight to determine material loss. The use of corrosion coupons, while viewed as a very good method of assessing corrosion, is typically expensive and inconvenient to use. In some instances, the structure needs to be taken out of service to remove the coupons from the service area, which is expensive and may have health and safety implications. As presently used, corrosion coupons do not give any early warning of impending failure until they are retrieved and examined.

Corrosion on the internal wall of oil and gas pipelines occurs when the pipe wall is exposed to water and contaminants in the fluid product or internal gas atmosphere. The nature and extent of the corrosion damage that occurs are functions of the concentration and particular combination of various corrosive constituents within the pipe, as well as the operating conditions of the pipeline. The impact of this contamination is the loss of pipe wall thickness that can result in pipe cracking and rupturing.

Similar degradation issues exist on the exterior surfaces of buried pipelines, where sacrificial coupons may be placed on the surface of the pipe and periodically removed for inspection and analysis. Similarly, other underground concrete building structures, underwater structures and the like are susceptible to corrosion and general metal loss due to surrounding environmental conditions that are monitored with the use of such coupons. Regardless, the current methods of coupon removal and replacement are fraught with measurement errors.

Two common methods of measuring the internal wall integrity are with (1) sacrificial metal "coupons" placed into the pipe's product stream that can be periodically removed and examined to determine the amount of metal loss which is then extrapolated as a representation of the pipe's internal condition, or (2) electrical resistance probes, which are inserted into the pipe's product stream and monitor the rate of corrosion of an exposed sample of metal through the change of resistance of an electrical current applied to the probe. Sample measurements are taken over a period of time with an electrical current measurement meter. Changes in resistance are translated into metal loss that yields the amount of loss over a period of time (typically, mils per year).

Both methods are considered to be relatively inaccurate, yield inconsistent readings, and create handling challenges. Thus, there remains a need within the industry for an improved method and apparatus for monitoring pipeline and storage tank corrosion.

SUMMARY

The ultrasonic corrosion coupon probe of the present invention solves many of the monitoring accuracy and handling problems through the use of one or more piezoelectric ultrasonic testing (UT) transducers integrated into a sacrificial, replaceable coupon. UT transducers are known to the non-destructive testing industry as one of the most accurate, repeatable and precise methods of determining material degradation and material loss. UT transducers have not been used in connection with sacrificial coupons, at least in part, because of the inability to effectively secure an ultrasonic transducer to a coupon for long periods of time. The connection interface between the UT transducer and the coupon changes over time, e.g., by evaporation or other chemical or physical changes, and as a result the ability of the transducer to transfer acoustic energy to the coupon is affected. The present invention solves this problem, and as a result UT transducers can be used to measure and monitor changes over time in a sacrificial coupon.

The present invention further solves the foregoing problems by providing a coupon-ultrasonic measurement system combined with one or more transducers for determining material loss. The system includes a sacrificial coupon; one or more transducers supported under the sacrificial coupon and responsive to electrical energy from a pulser/receiver; remotely-located drive circuitry for energizing and receiving energy from the transducers; an attachment mechanism for positioning the sacrificial coupon and transducer assembly into a pipe or tank or adjacent to a pipe or tank; and processing and memory means for producing the excitation pulse, receiving the transmitted pulse, processing the signal to determine material thickness, and storing the resultant material thickness values for display and tracking.

A sacrificial metal coupon is provided with one or more ultrasonic transducers which, when excited by a pulser-receiver excitation pulse, determines the thickness of the coupon and its rate of change over time. The sacrificial metal coupon ultrasonic transducer assembly can be inserted into the liquid stream of a pipe, under or inside of a tank, underground or underwater, or inserted into structures where absolute material loss values or material loss rate of change is being monitored. In order to characterize the type of metal loss due to corrosion or erosion, the excitation pulse can be a pulse-echo or chirp pulse and one transducer can insonify the coupon and the second transducer can receive the transmission a fixed distance away for further analysis. The use of ultrasound to measure metal loss in a sacrificial coupon minimizes the inaccuracy of traditional sacrificial coupon metal loss measurements and provides for a more convenient and safe method for determining coupon integrity.

The coupon-ultrasonic material measurement system can also be used to evaluate the loss of integrity due to chemical attack, where the chemical attack can be associated with change in the exposed liquid product quality or a change in process conditions. Additionally, the UT coupon assembly can be configured with a reference electrode, e.g., CuCuSo4 material, used to simultaneously measure the effectiveness of neighboring electromagnetic fields generated by cathodic protection impressed current systems One aspect of the invention is a corrosion coupon probe including: an elongated body adapted for receiving sensors, receivers, transmitters, electrical components, or connectors for altering the configuration of the elongated body; a collar secured to the elongated body for fastening the elongated body to one or more threaded extensions; a coupon holder member connected to the elongated body and adapted for receiving an ultrasonic testing (UT) transducer; one or more UT transducers secured to the coupon holder member; an acoustic couplant positioned adjacent the one or more UT transducers; a sacrificial coupon connected to the coupon holder member such that the sacrificial coupon is adjacent the acoustic couplant; an attachment body for inserting the sacrificial coupon into a liquid environment; and a reference electrode attached to the elongated body for simultaneously measuring corrosion rate of the sacrificial coupon and an electromagnetic field created by an impressed current cathodic protection system.

A second aspect of the invention is a corrosion coupon probe including: a sacrificial coupon; one or more UT transducers; and an acoustic couplant, wherein the one or more transducers are connected to the sacrificial coupon and the acoustic couplant is positioned between the sacrificial coupon and the one or more UT transducers.

A third aspect of the invention is a corrosion monitoring system including: a corrosion coupon probe having (i) a sacrificial coupon, (ii) one or more UT transducers, and (iii) an acoustic couplant, wherein the one or more transducers are connected to the sacrificial coupon and the acoustic couplant is positioned between the sacrificial coupon and the one or more UT transducers; processing means for producing an excitation pulse, for receiving a transmitted pulse from the sacrificial coupon, and for processing signals to determine sacrificial coupon material thickness; and memory means for storing material thickness values determined by the processing means.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION

Figure 1:
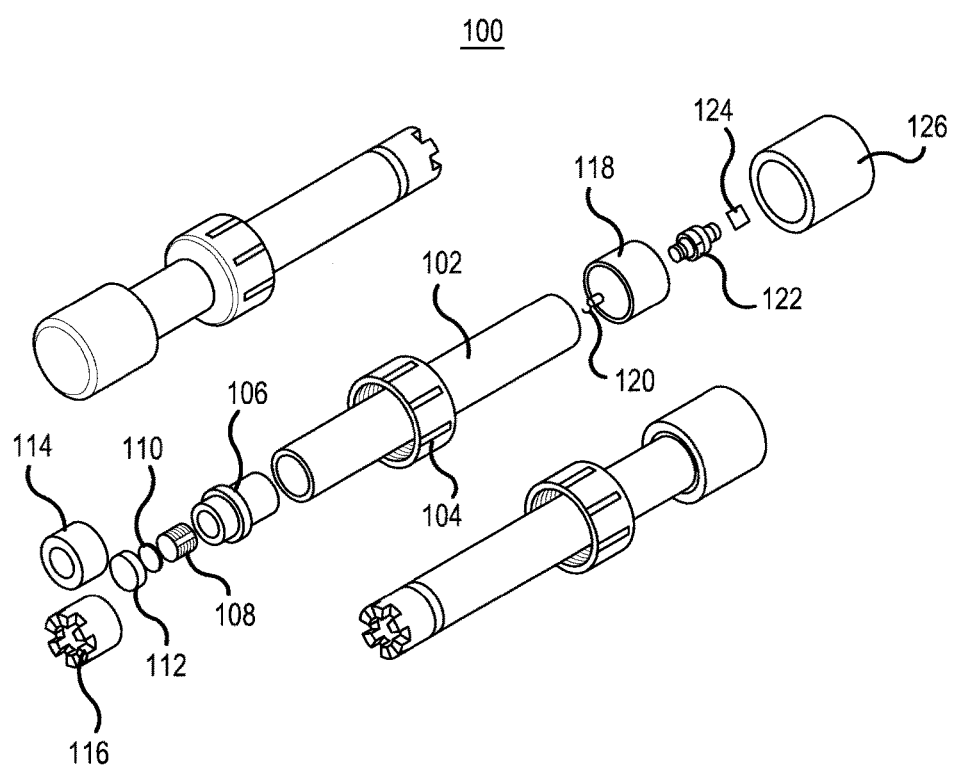
FIG. 1 is an exploded view of an ultrasonic corrosion coupon probe.

Referring generally to FIG. 1, there is shown an embodiment of a corrosion coupon probe (probe) 100 of the present invention. The probe 100 includes an elongated body (body) 102 that is adapted for receiving sensors and/or transmitters, electrical components, and various connectors for configuring the body 102 depending on the intended use of the probe 100. The body 102 optionally but preferably includes a collar 104, which can be used to fasten the body 102 to one or more threaded extensions. For example, the body 102 of the probe 100 can be fastened to a threaded extension protruding from an atmospheric storage tank (AST), or more than one body 102 can be combined to create a longer probe 100.

A coupon holder member 106 can be positioned in one end of the body 102 for securing a transducer in the probe 100. A first end of the coupon holder member 106 can be inserted into the body 102. The second end of the coupon holder member 106 is adapted for receiving a transducer and can include corresponding threads or other means for securing a transducer to the coupon holder member 106, such as press-fitting, a detent ball, clasp, etc.

An ultrasonic transducer assembly (transducer assembly) 108, comprising a piezoelectric chip, can be secured within the second opening in the coupon holder member 106. An acoustic couplant 110 is positioned adjacent the transducer assembly 108, and a sacrificial coupon (coupon) 112 is positioned against the couplant 110 on the side opposite the transducer assembly 108.

The coupon 112 material can be of one or more types of metal or non-metal that are subject to loss of integrity due to corrosion or erosion and where the loss and rate of loss can be precisely measured with the use of ultrasound transducers attached to the coupon material. In an alternative embodiment, the coupon material can be of one or more types of metal or non-metal that are subject to loss of integrity due to chemical attack and where the chemical attack can be associated with change in the exposed liquid product quality or a change in process conditions. In yet another alternative embodiment, the coupon material can be of one or more types of metal or non-metal that are subject to loss of integrity due to corrosion, erosion or chemical attack and where the electrical pulses of one or more transducers can be used to induce one or more different mechanical wave patterns which can be used to characterize the amount and type of material loss on the surface of the coupon material.

A coupon cap 114 can be secured to the coupon holder member 106 with corresponding threads or other suitable securing means such as press-fitting, a detent ball, clasp, etc. An alternative embodiment of a coupon cap 116 also is shown. The coupon cap 114 or 116 secures the transducer assembly 108, acoustic couplant 110, and coupon 112 within the coupon holder member 106, which is connected to a first end of the body 102.

A reference electrode 118 can be positioned in the second end of the body 102. The reference electrode 118 optionally but preferably is adapted for receiving an end cap or protective cover and can include corresponding threads or other securing means such as press-fitting, a detent ball, clasp, etc. The reference electrode 118 further can include a ground wire with an outside attachment point 120. One or more external electronic connectors 122 and an RFID tag 124 can be connected to the reference electrode 118. A protective cover 126 can be secured to the second end of the body 102.

The probe 100 can be placed near or offset from a surface it is designed to monitor. The coupon 112 is used as a surrogate to extrapolate the corrosion, pitting, metal loss, etc. of the pipe or other structure being monitored. The changes to the coupon 112 are representative of the changes to the pipe or other structure being monitored, and the condition of the structure being monitored can be determined indirectly by monitoring the status of the coupon 112. A data logger (not shown) can contain software to pulse and acquire the UT information, prepare the data for subsequent analysis within the data logger, or transmit the data wirelessly to a remotely located receiver, and organize the data within a database for future analysis.

Figure 2:
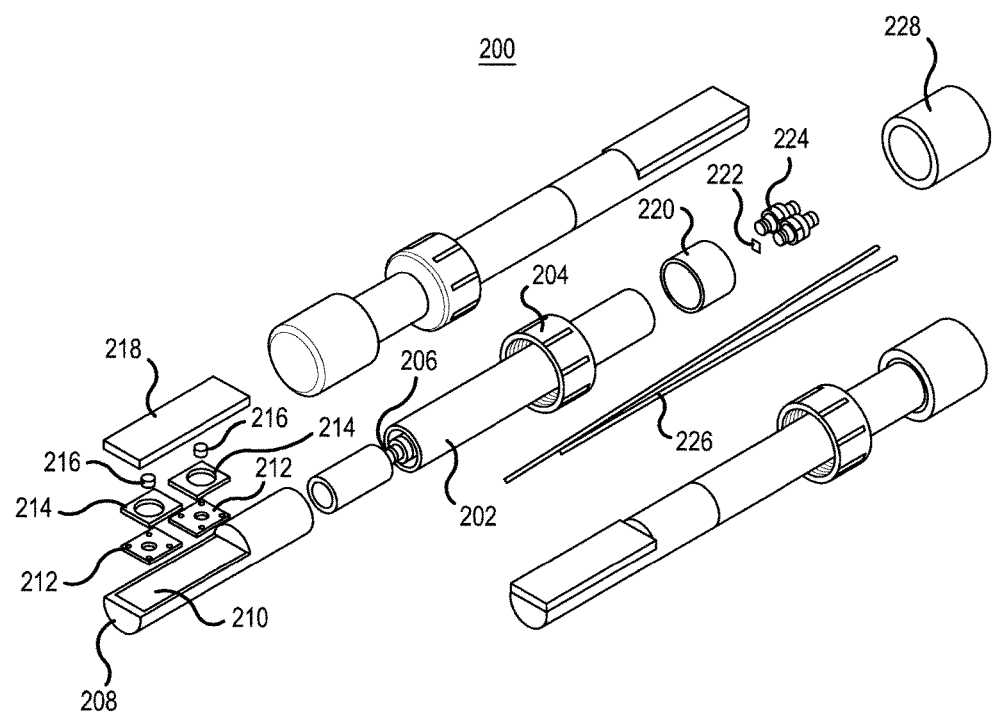
FIG. 2 is an exploded view of an alternative embodiment of an ultrasonic corrosion coupon adapted for use with an existing sacrificial coupon fitting.

Referring generally to FIG. 2, there is shown an alternative embodiment of a corrosion coupon probe 200 of the present invention. The probe 200 includes an elongated body (body) 202 that is adapted for receiving sensors and/or transmitters, electrical components, and various connectors for configuring the body 202 depending on the intended use. The body 202 optionally but preferably includes an internal electronic connector 206 and a collar 204, which can be used to fasten the body 202 to one or more threaded extensions. For example, the body 202 of the probe 200 can be fastened to a threaded extension protruding from an atmospheric storage tank (AST), or more than one body 202 can be combined to create a longer probe 200.

A coupon holder member 208 can be secured to a first end of the body 202. The coupon holder member 208 optionally but preferably includes an encapsulation material 210 and is adapted for receiving a coupon and other corrosion monitoring hardware. More specifically, one or more transducer assemblies 212, each comprising a piezoelectric chip, can be positioned atop the encapsulation material 210 on the coupon holder member 208. One or more retainers 214, which correspond to the one or more transducer assemblies 212, can be placed on top of the transducer assemblies 212. The transducer assemblies 212 can be affixed to the retainers 214 chemically, e.g., by using glue or other adhesive materials, or mechanically by snapping or press-fitting the transducer assemblies 212 and retainers 214 together. One or more acoustic couplants 216, which correspond to the one or more transducer assemblies 212, can be positioned on top of the one or more retainers 214 and in communication with the transducer assemblies 212.

A coupon 218, also in communication with the acoustic couplants 216, is positioned on top of the retainers 214 and is secured to coupon holder member 208. The coupon 218 material can be of one or more types of metal or non-metal that are subject to loss of integrity due to corrosion or erosion and where the loss and rate of loss can be precisely measured with the use of ultrasound transducers attached to the coupon material. In an alternative embodiment, the coupon 218 material can be of one or more types of metal or non-metal that are subject to loss of integrity due to chemical attack and where the chemical attack can be associated with change in the exposed liquid product quality or a change in process conditions. In yet another alternative embodiment, the coupon 218 material can be of one or more types of metal or non-metal that are subject to loss of integrity due to corrosion, erosion or chemical attack and where the electrical pulses of one or more transducers can be used to induce one or more different mechanical wave patterns which can be used to characterize the amount and type of material loss on the surface of the coupon material.

Figure 6:
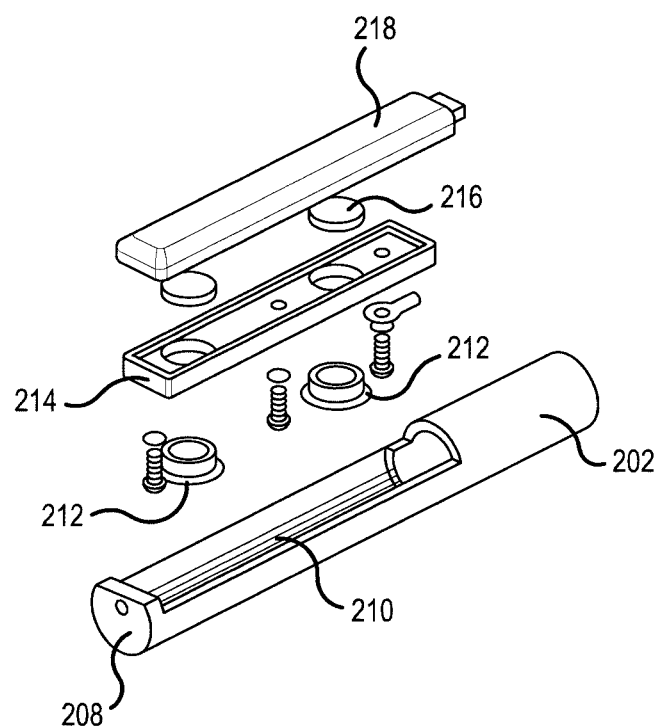
FIG. 6 is an exploded of an alternative embodiment of an ultrasonic corrosion coupon.

As shown in FIG. 6, in one of many alternative embodiments of the invention the retainer 214 can be a single piece, which provides extra rigidity to the transducer assemblies 212. The transducers 212 can be connected to a bottom surface of the coupon 218 by machine screws or other fastening means. The acoustic couplants 216 are placed between the face of the piezoelectric chips in the transducer assemblies 212 and the bottom surface of the coupon 218. As the machine screws are tightened, the couplants 216 are compressed to a fixed point that will not alter the quality of the UT transducer A-scan. The transducer assemblies 212 optionally but preferably are sealed and are waterproof so the probe 200 can be positioned anywhere to monitor metal loss remotely using ultrasound as long as the wiring is properly sealed.

A reference electrode 220 can be positioned in the second end of the body 202. The reference electrode 220 optionally but preferably is adapted for receiving an end cap or protective cover and can include corresponding threads or other securing means such as press-fitting, a detent ball, clasp, etc. An RFID tag 222 can be connected to the reference electrode 220, and one or more external electronic connectors 224 can be included and adapted for receiving an electronic connector extension cable 226 or an umbilical. An umbilical can be used as a conduit that houses wires necessary for providing electrical pulses to and from a pulser/receiver, which can be either attached to or located remotely from, a coupon-ultrasonic material measurement system of the present invention. A protective cover 228 can be secured to the second end of the body 202.

The probe 202 can be placed under a mechanical structure, such as an aboveground storage tank. The coupon 218 can be used as a surrogate to extrapolate the corrosion, pitting, metal loss, etc. of the storage tank or other structure being monitored. The changes to the coupon 218 are representative of the changes to the underside of the tank, e.g., its metal loss, and the condition of the tank floor or other structure being monitored can be determined indirectly by monitoring the status of the coupon 218. The probe 202 also can include a reference electrode 220, which can be used to measure potential difference of the impressed current impinging on the pipe or tank bottom, for instance, and ground. A data logger (not shown) can contain software to pulse and acquire the UT information, prepare the data for subsequent analysis within the data logger, or transmit the data wirelessly to a remotely located receiver, and organize the data within a database for future analysis.

Figure 3:
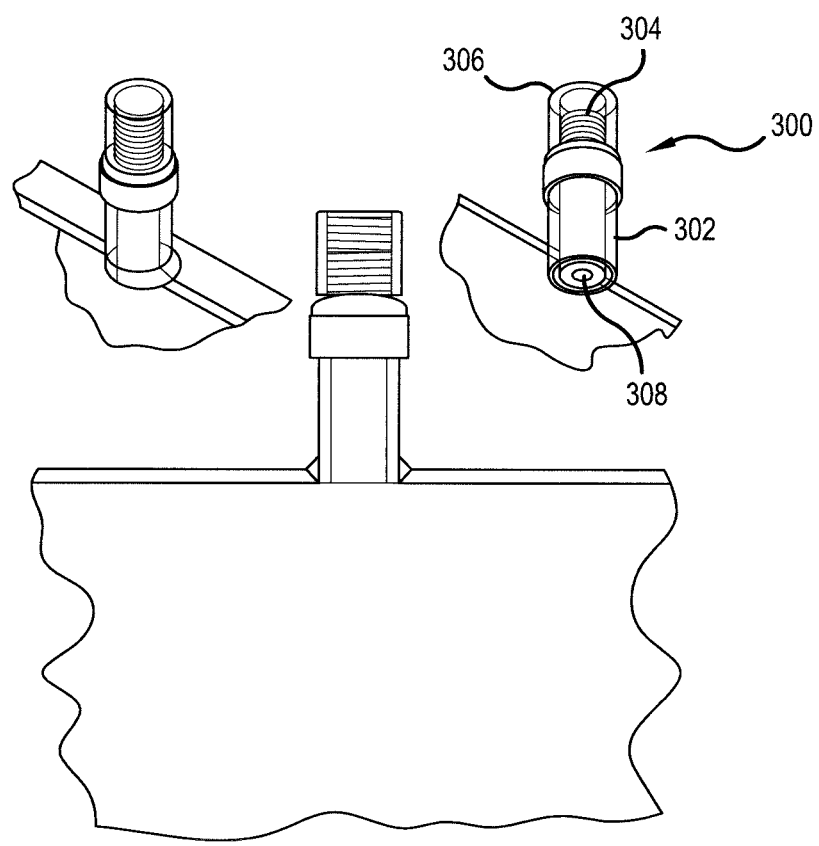
FIG. 3 is an exploded view of an alternative embodiment of an ultrasonic corrosion disc coupon adapted for use within the liquid stream of a pipe.

As shown in FIG. 3, a corrosion coupon probe 300 can be adapted for use in a pipe or pipeline. The probe 300 optionally but preferably has a stainless steel housing 302 and a connector 304 with a sealed cap 306 for protecting data retrieval and transmission means. A corrosion coupon disc 308 is used to represent and monitor the metal loss of the inner wall of the pipe.

Figure 4A:
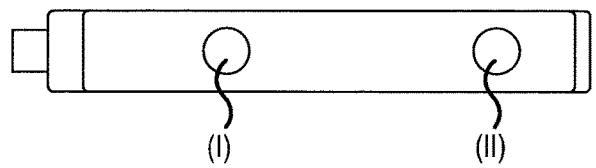
FIGS. 4A-4E illustrate the five (5) modes of electrical to mechanical energy conversion used to characterize the amount of and type of material loss.
Figure 4A:
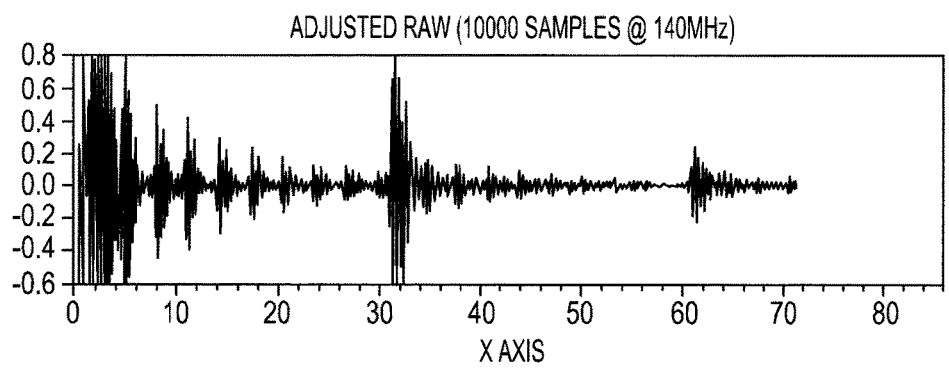

As shown in FIGS. 4A-4E, there are at least 5 modes of mechanical energy signal processing that may be applicable to the present invention. The first mode, shown in FIG. 4A, is created by the compression of the material directly under the UT transducer that reverberates from the front surface of the coupon to the back surface. The thickness of the coupon material can be determined by dividing the signal travel time from surface-to-surface in the coupon material by the speed of sound of the material.

Figure 4B:
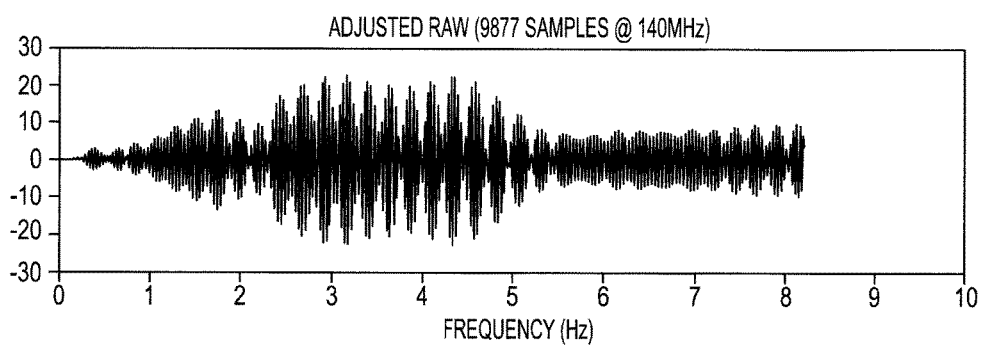

The second mode, shown in FIG. 4B, of mechanical energy created by the UT transducer is referred to as a bulk wave. The bulk wave is created by one UT transducer, Transducer(i), that is received by the adjacent UT transducer, Transducer(ii), located a fixed distance from the transmitting UT transducer. The energy transmitted into the coupon material will change as a function of any change in the mechanical integrity of the coupon. Changes in mechanical integrity can be in the form of overall reduction in thickness, the appearance of localized pitting or the appearance of cracks. The total energy created by the bulk wave can be referred to as the root mean squared (RMS). The RMS value of a set of continuous-time waveforms is the square root of the arithmetic mean of the squares of the values, or the square of the function that defines the continuous waveform. The formula for a continuous function (or waveform) f(t) defined over the interval $T_1 \le t \le T_2$ is:

$$f_{rms} = \sqrt{\frac{1}{T_2 - T_1} \int_{T_1}^{T_2} [f(t)]^2 dt},$$

and the RMS for a function over all time is $$f_{rms} = \lim_{T \to \infty} \sqrt{\frac{1}{T} \int_0^T [f(t)]^2 dt}.$$

Figure 4C:
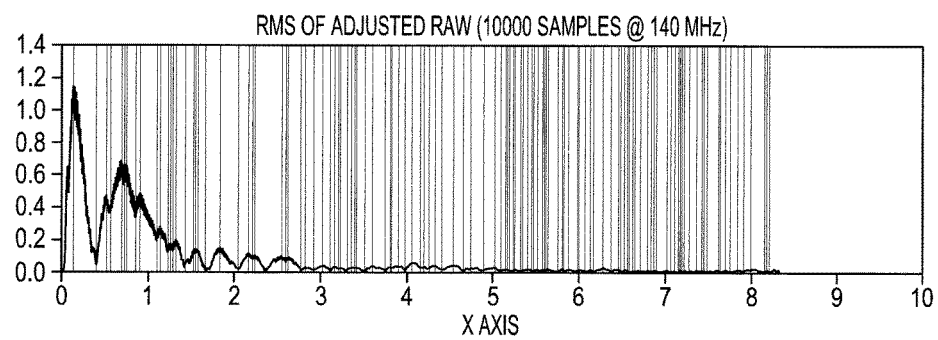
Figure 4D:
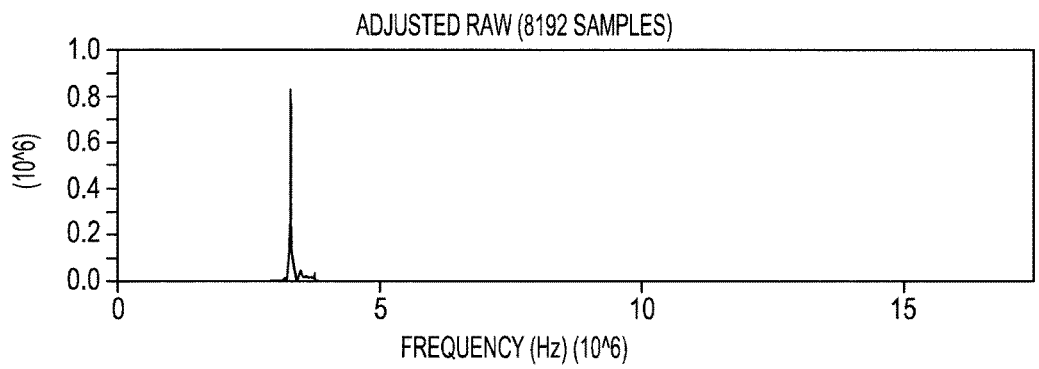

The effective RMS voltage (or power) of one or more sinusoids can be obtained without the use of calculus and can be calculated by squaring a waveform, taking the mean of the squared waveform and then computing the square root, as given by:

$$V_{rms} = \sqrt{\text{mean}[v(t) * v(t)]} = \sqrt{\frac{\text{area under the curve of } [v(t) * v(t)]}{\text{observation length}}}$$

where the observation length is the period, or integer multiple of the period, for as long as possible for the aperiodic signals generated by the piezoelectric-induced mechanical waves in the coupon. The total RMS value for any bulk wave can be measured and the resultant RMS return can be displayed as depicted in FIG. 4C.

An additional way to provide greater information about the current condition of the coupon and any change due to external factors is through the frequency response of the coupon. The total frequency response associated with the mechanical vibrations produced by the coupon as a result of the piezoelectric transducer, shown in FIG. 4D, can provide information about changes in the coupon's integrity. A fast Fourier transform (FFT) algorithm can be used to convert components of a signal, in this case mechanical vibrations, from its time domain to a representation in the frequency domain. There are a number of different types of FFT formulas but the most common one used for discrete Fourier analysis is noted below and is used in the current embodiment of the coupon-ultrasonic material measurement system:

$$X_k = \sum_{n=0}^{N-1} x_n e^{-i 2\pi k \frac{n}{N}} \quad k = 0, \ldots, N-1.$$

Figure 4E:
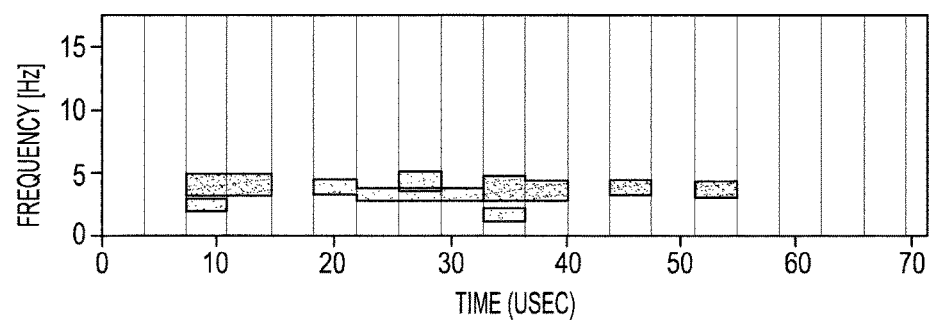

Finally, another method of detecting change in the integrity of the coupon is through the use of a spectrographic analysis as shown in FIG. 4E. In the this case, the mechanical energy resulting from the vibrations produced by the coupon as a result of the piezoelectric transducer can be displayed in terms of the coupons frequency response distributed over time.

Figure 5:
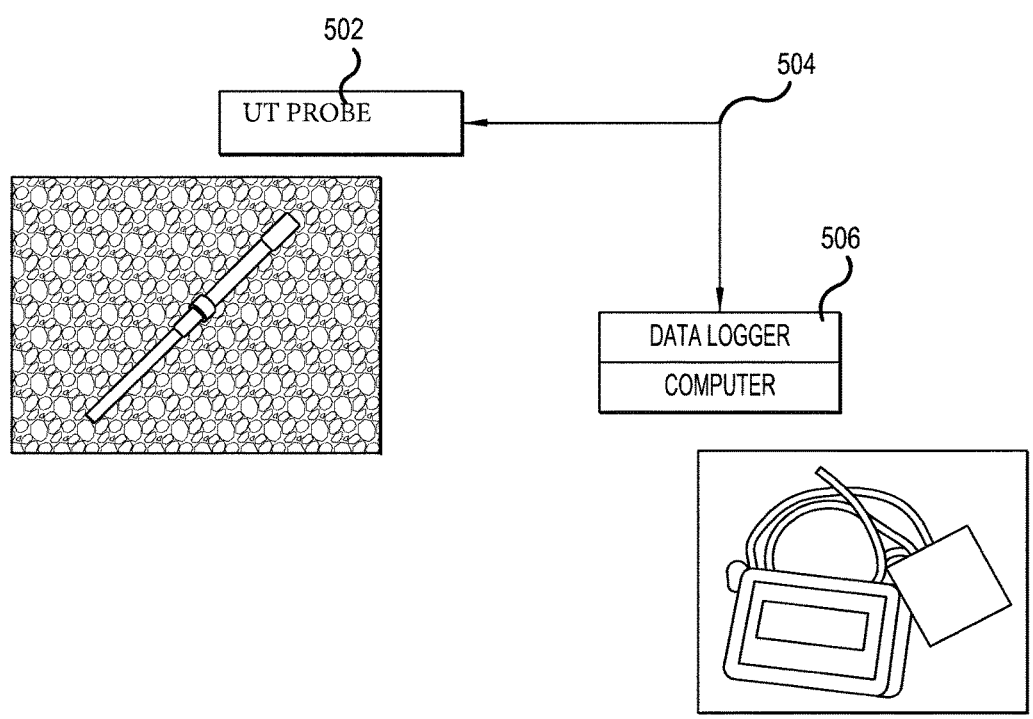
FIG. 5 is a block diagram of the total coupon probe inspection system showing the relationship between the data logger and the coupon probe assembly.

As shown in FIG. 5, a UT probe 502 can include an umbilical 504 in communication with a data logger 504, which optionally but preferably is interfaced with a general purpose computer or has independent processing means, and further includes a pulser/receiver unit. The umbilical 504 can transmit electrical energy, or pulses, created by the pulser/receiver in the data logger 506 to the probe 502. The umbilical 504 also can transmit an electrical representation of the return signal from one more transducers in the probe 502 back to the data logger 506. The data logger 506 can include or otherwise is in communication with external electronic connectors 122, 224 as shown in FIGS. 1 and 2, respectively.

In operation, piezoelectric UT transducers of the present invention convert pulses of electrical energy into an acoustic pressure wave (sound). The pressure wave is coupled to the surface of a coupon by a couplant material, such as silicone synthetic grease or cured silicone. Most of the energy is reflected from the front surface of the coupon due to the acoustic impedance discontinuity. Some energy enters the coupon plate, travels through the coupon plate and is reflected from the back surface of the coupon back towards the front surface. This reflection process continues. Energy is lost from the coupon plate boundary surfaces for each reflection. Energy lost at the front of the coupon travels back towards the ultrasound transducer where it is received and converted back to electrical energy. The electrical pulses received represent the two way acoustic front-to-back acoustic travel times. The thickness of the plate can be estimated by measuring the pulse-to-pulse travel time and dividing the travel time by the speed of sound in the coupon material. By searching for a reduction in the coupon plate thickness, plate corrosion or pitting can be located as discussed in more detail below.

FIG. 1 and FIG. 2 show two embodiments of the probe 100, 200. The probe 100 in FIG. 1 contains a single transducer 108 in the shape of a disc, which measures the loss of metal from the disc coupon 112. The probes 100, 200 can be placed near or on the mechanical surface it is designed to monitor or the probes 100, 200 can be inserted into the liquid stream within the pipe.

More than one UT transducer can be attached to, and integrated with, a coupon 208. As shown in FIG. 2, the probe 200 contains two transducers 212 that measure the loss of metal in two or more places on the coupon 208. Such a probe 200 can be inserted underneath an aboveground tank or immediately adjacent to an underground tank for measuring local metal integrity conditions such on tank shells or bottoms. Additionally, a ground reference electrode can be fastened to the probe 200 body 202 and can be used to measure the potential difference of the impressed current impinging on the pipe, or tank bottom, for instance, and ground. $CuCuSO_4$ electrodes are often used for such ground potential monitoring.

Coupons as contemplated herein can be made in different shapes, diameters, sizes, lengths, and made from different materials. The coupons can be placed under aboveground storage tanks, adjacent to underground storage tanks, buried piping and pipelines, on the surface of a buried pipe, or screwed into a pipe. UT measurements can be acquired manually with a hand-held meter, or the measurements can be acquired electronically and transmitted via built-in ultrasound pulser/receiver electronics and radios to remote locations.

Multiple methods of determining material thickness and material loss can be integrated into software used to acquire coupon integrity information, including the ability of one transducer to transmit or receive information from another transducer attached to the coupon. The coupon can be attached to extensions for remote installations while retaining the easy-access data acquisition capabilities. A passive or active RFID tag can be integrated into the probe for automatic registration within a data logger of the probe's serial number and location (latitude/longitude) during UT data acquisition. The probe body can be screwed into a pipe for in-stream measurement, inserted under a tank or inserted within close proximity of the surface of buried pipelines and mechanical structures, and the probe can be submerged in a liquid.

CONCLUSION

While various embodiments of the present invention have been described above, it should be understood that they have been presented by way of example only, and not limitation. It will be understood by those skilled in the art that various changes in form and details may be made therein without departing from the spirit and scope of the invention. Thus, the breadth and scope of the invention should not be limited by any of the above-described exemplary embodiments.

What is claimed is:

1. A corrosion coupon probe, comprising:
    an elongated body;
    a collar secured to the elongated body for fastening the elongated body to one or more threaded extensions;
    a coupon holder member connected to the elongated body for receiving one or more ultrasonic testing (UT) transducers;
    one or more UT transducers secured to the coupon holder member;
    an acoustic couplant positioned adjacent the one or more UT transducers;
    a sacrificial coupon connected to the coupon holder member such that the sacrificial coupon is adjacent the acoustic couplant;
    an attachment body for inserting the sacrificial coupon into a liquid environment; and
    a reference electrode attached to the elongated body for measuring corrosion rate of the sacrificial coupon.

2. The corrosion coupon probe of claim 1, wherein the reference electrode is a $Cu-CuSO_4$ grounding electrode.

* * * * *